US012569369B2

(12) United States Patent
Vogelsang et al.

(10) Patent No.: US 12,569,369 B2
(45) Date of Patent: Mar. 10, 2026

(54) SYSTEM FOR LASER-BASED AMETROPIA CORRECTION, AND METHOD FOR THE ALIGNMENT THEREOF

(71) Applicant: Carl Zeiss Meditec AG, Jena (DE)

(72) Inventors: Hartmut Vogelsang, Oberweser (DE); Dan Zoltan Reinstein, London (GB); Christian Deutsch, Weimar (DE); Ingo Wundrich, Weimar (DE)

(73) Assignee: Carl Zeiss Meditec AG, Jena (DE)

( * ) Notice: Subject to any disclaimer, the term of this patent is extended or adjusted under 35 U.S.C. 154(b) by 525 days.

(21) Appl. No.: 17/996,814

(22) PCT Filed: May 21, 2021

(86) PCT No.: PCT/EP2021/063616
§ 371 (c)(1),
(2) Date: Oct. 21, 2022

(87) PCT Pub. No.: WO2021/239606
PCT Pub. Date: Dec. 2, 2021

(65) Prior Publication Data
US 2023/0201035 A1     Jun. 29, 2023

(30) Foreign Application Priority Data

May 24, 2020    (DE) ..................... 10 2020 206 423.7
May 24, 2020    (DE) ..................... 10 2020 206 426.1
Jul. 10, 2020    (DE) ..................... 10 2020 208 676.1

(51) Int. Cl.
*A61F 9/008*        (2006.01)
*A61F 9/009*        (2006.01)

(52) U.S. Cl.
CPC ...... *A61F 9/00804* (2013.01); *A61F 9/00814* (2013.01); *A61F 9/009* (2013.01);
(Continued)

(58) Field of Classification Search
None
See application file for complete search history.

(56) References Cited

U.S. PATENT DOCUMENTS 9,592,156 B2     3/2017  Huang
2005/0024586 A1*  2/2005  Teiwes ................... A61B 3/113
                                            351/209
(Continued)

FOREIGN PATENT DOCUMENTS

WO      2009033111 A2    3/2009
WO      2010028663 A1    3/2010

OTHER PUBLICATIONS

Krueger et al.: "Corneal Surface Morphology Following Excimer Laser Ablation With Humidified Gases," Archives of Ophthalmology, vol. 111, No. 8, pp. 1011-1152, Aug. 1993.
(Continued)

*Primary Examiner* — Michael T. Holtzclaw
(74) *Attorney, Agent, or Firm* — Pearl Cohen Patentanwälte PartGmbB; Michael McCandlish

(57)        ABSTRACT
A method for aligning a system for laser-based ametropia correction relative to a patient's eye to be treated is disclosed. Predefined pre-operative measurement data which characterize at least predetermined structures of the patient's eye is provided. The predetermined structures include a part of the patient's eye to be treated. In addition, the method includes measuring at least one part of the predetermined structures of the patient's eye using an OCT system immediately before and/or during treatment for ametropia correction of the patient's eye and providing OCT measurement data, and comparing the OCT measurement data and the predefined pre-operative measurement data and preparing comparative data. The method also includes ascertaining a position and/or orientation of the part of the patient's eye to be treated relative to the system and aligning the system
(Continued)

relative to the patient's eye using the ascertained position and/or orientation of the part of the patient's eye.

25 Claims, 4 Drawing Sheets

(52) U.S. Cl.
CPC ............... *A61F 2009/00846* (2013.01); *A61F 2009/00851* (2013.01); *A61F 2009/00857* (2013.01); *A61F 2009/00872* (2013.01)

(56) References Cited

U.S. PATENT DOCUMENTS

| | | | |
|---|---|---|---|
| 2011/0040292 A1* | 2/2011 | Riedel ................. | A61F 9/00802 606/5 |
| 2013/0226157 A1 | 8/2013 | Huang | |
| 2015/0031993 A1 | 1/2015 | Buckland et al. | |
| 2015/0141972 A1* | 5/2015 | Woodley ............. | A61F 9/00804 606/5 |
| 2016/0095752 A1* | 4/2016 | Srinivasan .......... | A61F 9/00834 606/6 |
| 2017/0189233 A1* | 7/2017 | Dewey ................ | A61F 9/00825 |

OTHER PUBLICATIONS

Atchison, "Handbook of Visual Optics vol. 1," Chapter 17, Ed. Pablo Artal, CRC Press Tayler & Francis Group, 2017.
International Preliminary Report on Patentability issued in PCT/EP2021/063616, to which this application claims priority, mailed Nov. 17, 2022, and English-language translation thereof.
U.S. Appl. No. 17/996,808, filed Oct. 21, 2022, Hartmut Vogelsang, Christian Deutsch, Ingo Wundrich, and Dan Z. Reinstein.
Nowakowski et al.: "Investigation of the isoplanatic patch and wavefront aberration along the pupillary axis compared to the line of sight in the eye," Biomedical Optics Express 240, vol. 3, No. 2, Feb. 1, 2012.
International Search Report by the International Searching Authority in PCT/EP2021/063616, to which this application claims priority, mailed Sep. 15, 2021, and English-language translation thereof.
Written Opinion by the International Searching Authority in PCT/EP2021/063616, to which this application claims priority, mailed Sep. 15, 2021.
Intention to grant issued in EP 21 729 236.6, which is a counterpart hereof, mailed on Oct. 8, 2025, and English-language machine translation thereof.
Decision to grant issued in EP 21 729 236.6, which is a counterpart hereof, mailed on May 21, 2025, and English-language machine translation thereof.

\* cited by examiner

SYSTEM FOR LASER-BASED AMETROPIA CORRECTION, AND METHOD FOR THE ALIGNMENT THEREOF

CROSS REFERENCE TO RELATED APPLICATIONS

This application is a national stage application of international patent application PCT/EP2021/063616, filed May 21, 2021, designating the United States and claiming priority from German patent applications DE 10 2020 206 423.7, filed May 24, 2020, DE 10 2020 206 426.1, filed May 24, 2020, and DE 10 2020 208 676.1, filed Jul. 10, 2020, and the entire content of all applications is incorporated herein by reference.

TECHNICAL FIELD

The present disclosure relates to laser vision correction (LVC) systems, that is to say systems for vision correction by means of laser radiation, with the correspondingly included treatment laser emitting in the ultraviolet range and an example of said laser beam being an excimer laser or solid-state laser with wavelengths between approximately 193 nm and 213 nm and/or being in the form of femtosecond or picosecond lasers. These systems are typically pulsed systems, that is to say not systems that emit continuous waves. Such LVC systems are used to process the cornea of a patient's eye starting from its surface or to process a volume under a folded-away surface of the cornea of the patient's eye starting from the exposed surface, in each case by means of photoablation. Alternatively, such systems can be used to separate a lenticule in the cornea such that said lenticule can subsequently be removed. The disclosure further relates to corresponding methods for the alignment or centration of such systems. LVC systems are also simply denoted "systems" in the present disclosure. Provided nothing else is specified explicitly, a system can therefore be a UV laser-based system or a femtosecond laser-based/picosecond laser-based system.

BACKGROUND

Conventional LVC systems, for example the MEL systems by Carl Zeiss Meditec AG, the Amaris systems by Schwind eye-tech solutions GmbH or the Micron systems by Excelsius Medical GmbH, are systems for vision correction that have been successfully employed for a long time. The present disclosure proposes and explains further improvements for such systems.

Conventional LVC systems typically provide for a rigid laser beam guiding system. Although this facilitates safe laser beam guidance, it requires that the patient on a patient couch is moved under a fixed system aperture in x, y, z coordinates by means of said patient couch until the patient's eye intended to be treated is correctly positioned in relation to the optical axis of the system. An exception is formed by the system described in US 2013/0226157 A1, in which the laser arm, rigid per se, is positioned as a whole over the patient, albeit in a manner which still requires the positioning of the patient by way of the patient couch. For safety reasons, the latter frequently requires the patient couches to be electrically and/or mechanically connected to the laser base unit, which in turn requires a system certification and large amounts of space.

Additionally, there usually is a manual, static alignment of the eye in relation to cyclorotation in conventional LVC systems, i.e., without an automatic correction with the aid of registration data, by rotating the patient's head on the couch under visual monitoring. This limits the obtainable accuracy and may then lead to unwanted deviations if there is a rotation of the head of the patient during the treatment without a correction of the cyclorotation caused thereby.

Moreover, contact interfaces for affixing the eye are known in some conventional LVC systems. In such LVC systems, for example as described in US 2013/0226157 A1 and U.S. Pat. No. 9,592,156 B2, these are only implemented for eye stabilization purposes and do not adopt an active role. By contrast, work is carried out entirely without contact interfaces in many systems.

Large working distances between laser exit aperture and eye were realized with the introduction of spot-scanning LVC systems. This was also implemented against the background of using microkeratomes, which were used with the patient on the patient bed of the system, in order to cut the LASIK flap, that is to say an opening in the cornea that can be folded to one side. Among other things, this also required great working distances. Eye trackers for registering and compensating the eye movements were introduced at a later stage, and hence the eye movements during the ablation, which arose due to an unaffixed eye, were compensated. The overall optical system concept accompanying this—which in principle is very similar in the various systems—may also be considered to be disadvantageous.

Various technical challenges arise in relation to eye tracking during the application thereof. Overall, the registration speed for the eye movement is limited and the adjustment of the scanner mirrors for correcting the pulse coordinate requires a finite amount of time. In the context of the system performance, the response to the eye movement ("response time") is generally delayed and hence limited in terms of accuracy. In the case of conventional, fast eye tracker systems (with a repetition rate of approximately 1000 Hz), this is sufficient for the lateral correction (x, y displacement; "1st and 2nd eye tracking dimension"). However, even the fastest conventional systems may lead to limitations, especially if the eye tracker speed is below the limit for the scanning frequency. In some systems, a prediction about the future movement of the eye is made on the basis of the preceding movement trajectories of the eye ("7th eye tracking dimension"). This is possible within the scope of an approximation since eye saccades/nystagmus correspond to statistical movements of the eye in the broadest sense. This also highlights the fact that an increase in the repetition rate is connected with technical challenges with conventional technology, even though this would be of interest for certain applications and in certain ablation timeframes (thermal controlled/mild ablation).

Moreover, purely lateral tracking can be a limitation since the rotation of the eye about the z-axis ("dynamic cyclorotation;" "6th eye tracking dimension") and the roll movements about the horizontal and vertical eye axes ("3rd and 4th eye tracking dimension") have to be taken into account to achieve a best-possible accuracy. Moreover, the distance (z-distance) to the laser exit aperture may also vary, which can likewise be compensated for by appropriate tracking (5th eye tracker dimension).

Despite all technical intricacies and correction options, the conventional systems are limited in reacting exactly to a change in the eye position in some cases: The limited quality of the registration and the speed of the registration and correction may have a decisive influence in this case. However, the influence on the refractive results is normally very small and hardly detectable.

However, further challenges may arise with the eye tracking in the case of uncooperative patients, in the case of whom there are fixation instability, nervousness, cognitive deficits or problems with perceiving the fixation target. In some cases, it may appear necessary to the eye surgeons to manually affix the eyes of the patient during the ablation by means of a clamp and/or a foam spatula in order to enable a precise ablation. This may serve to prevent an eye movement outside of what is known as a (limited) "eye tracker hot zone" because the system may otherwise have to be stopped.

In the case of LVC systems, too, it is necessary to ensure that the production of prismatic errors by way of the eye tracker is avoided. If this is not ensured, this may lead to the unwanted case of the ablation profiles not being applied in the correct plane, that is to say not on the surface normal, i.e., perpendicular to the visual axis. This may be promoted by virtue of the patient preferably fixating in a largely fixed but "incorrect" direction, that is to say, e.g., permanently looking in a fixed direction that does not correspond to the center of the "fixation cloud" (depending on refractive deficit and treatment duration, the patient can no longer see the fixation target in focus during the operation).

FIG. 1 shows a schematic representation of the principle of how prismatic correction errors (tip/tilt) arise as a result of the insufficiently accurate use of an eye tracker when the patient does not fixate on the center of the "fixation cloud." In this case, FIG. 1 depicts a patient's eye 10 with cornea 12 and fovea 14, and the optical axis 16 of the patient's eye or the visual axis 16, an ablation profile 18, a scanning system 20 and a fixation element 22, on which the patient should fixate with their gaze.

If the patient does not fixate their eye 10 on the center but, for example, on an edge region of the fixation element 22, this may have as a consequence that the ablation profile 18 is not correctly applied along the necessary treatment axis (e.g., visual axis 16; defined by the ophthalmic pole (OP) and fixation of the patient) and hence not applied normally with respect to the visual axis. The relationships are depicted with much exaggeration in FIG. 1.

Eye trackers also do not work equally reliably for all eyes since some eye colors may have an insufficient contrast. Should the use of the eye tracker not be possible, eye surgeons may be compelled to terminate the operation or continue without eye-tracker assistance, but this places greater demands on the capability of the surgeon.

Constant ambient conditions above the operation site often cannot be set, or can only be set to a very qualified extent, by conventional systems. However, it is known that the influence of varying ambient conditions, for instance the humidity and changes in the hydration state of the cornea accompanying this, the composition of the air (in the case of evaporation of solvents for example) or the temperature, may be significant on the refractive results. It is also known to be advantageous to ensure that the hydration state of the cornea is maintained during the ablation, or to avoid drying out of said cornea (see, e.g., R. R. Krueger, M. Campos, X. W. Wang, M. Lee, P. J. McDonnell, "Corneal Surface Morphology Following Excimer Laser Ablation With Humidified Gases", Arch Ophthalmol. 111, 1993). Typically, a distinction should be made between two effects for the hydration: a) the physiological differences in the hydration of the cornea as a distribution over various patients, and b) the maintenance of the hydration during the ablation itself. Both influences lead to an increased variation in the refractive result (for example via an increased variation in the "attempted vs. achieved" prediction). The literature contains many investigations in this respect. Accordingly, the influence of the hydration of the cornea is significant in particular.

A further factor that influences the refractive results is related to the amount and accumulation of ablation products ("debris") over the ablated cornea, that is to say the operation site. It is sufficiently well known that the radiated-in UV ablation pulses may be absorbed and scattered in the debris. This may uncontrollably modify the effective pulse fluence, which decisively controls the ablation process. This may lead to significant fluence deviations in the sequence of the ablation pulses. In the case of myopia treatments, this may lead to the unwanted creation of central steepening of the cornea post surgery (what are known as central islands). Therefore, conventional systems usually have aspiration means or a combined air supply and aspiration means for the debris. However, a large distance from the supply or discharge lines may be an obstacle to an effective removal of debris. In principle, a replacement of the entire air volume above the cornea to be treated between successive pulses in the case of pulse repetition rates between 500 Hz and 1000 Hz would be advantageous. Otherwise, this may lead to "skew" ablations and hence, for example, to induced coma or SIA (surgically induced astigmatism)—in the case of non-optimal or directed aspiration of the ablation products—which should be avoided.

Moreover, dehydration of the cornea should be avoided in the case of systems which additionally supply air. As a rule, this can only be avoided to a restricted extent. Overall, the operation site cannot be readily decoupled from the remaining operative surroundings (e.g., airflows in the theater) as a result of the open arrangement of conventional systems either.

The sterile and secure placement of the flap is of extraordinary importance for a LASIK procedure. Typically, a flap is only 100 μm thick and, following the LASIK incision, only fastened to the cornea by way of a very narrow "hinge." Maintaining the hydration of the flap is very important for pathological reasons and also for maintaining the shape of the flap since dehydrated flaps may shrink within seconds. In certain circumstances, a shrunken flap may suffer from accuracy of fit in relation to the stromal bed post treatment (which may also be due to the change in shape of the stroma surface by the ablation), which may lead to postsurgical complications (e.g., "epithelial ingrowth") if not given due consideration. Where possible, flaps should not be bent, pulled or otherwise stressed either. Hence, experts these days hardly still use the "calzone technique" that was employed in the past. Moreover, the flap should also be prevented from coming to rest in possibly non-sterile regions of the eye. Despite the sterile preparation of the eye, this may nevertheless occur, for example as a result of the tear film or contact with non-sterile parts of the lids.

In want of a solution that is integrated in the conventional systems, some users cut their own flap repositories from sterile foam spatulas (or similar materials), which are then moistened and serve as safe and sterile rest for the sensitive flap. Thus, a solution is sought after in order to improve this.

On account of the relatively large working distances Δ of conventional LVC systems, there is hardly a difference there in the focusing plane. Therefore, these ULV-LVC systems can be considered to be virtually telecentric on the image side. In the case of conventional LVC systems, which typically have a working distance (distance between equipment exit aperture contour and eye) of approximately 250 mm, the rays are incident on the cornea at a significant angle since the typical radius of curvature RC of the human eye is approximately 7.86 mm. This has the further disadvantage that the optical acceptance angle for the return of reflections at the cornea to the optical system is also very small, leading to significant limitations of current systems and, as a rule, precluding, or reducing to a minimum, a use of the reflections at the cornea.

Now, further disadvantages of conventional LVC systems are described, which result largely directly from the optical concepts and the geometry of the ablation resulting therefrom.

As a result of an oblique incidence of the laser radiation on the cornea, there are losses in the fluence, that is to say the energy density of the laser pulse, which is decisive for the ablation, in conventional systems. Two effects should be considered here: The losses from deviations of the pulse ablation footprint as a result of the local geometry of the cornea at the location of the ablation pulse ("geometry factor") and the Fresnel losses when radiating light at interfaces with different refractive indices (air, cornea), which can be calculated using the Fresnel equations. These effects are sufficiently well known in the prior art.

The pulse ablation shape (corresponds to the ablation-effective fluence distribution of the radiated-in ablation laser pulse in a plane perpendicular to the direction of incidence) is deformed by the geometry of the irradiation of the cornea to form the "pulse ablation footprint on cornea", and hence the fluence distribution changes vis-à-vis the radiated-in pulse ablation shape.

The Fresnel losses can be calculated with the aid of the Fresnel equations with knowledge of the refractive indices of the air and cornea (or stroma) and the angles of incidence, with the polarization of the laser radiation having to be taken into account.

The use of back reflections from the cornea of the patient's eye for analysis purposes and, in particular, for centration purposes is only possible to a very restricted extent, or even entirely impossible, on account of the large working distance of conventional LVC systems from the patient's eye and the small acceptance angle of the focusing optical unit accompanying this. The influence of an inaccurate centration is known and has already been discussed multiple times in the literature. The view often taken that centration errors, that is to say deviations of the ablation center from the target positions on the cornea, like typically by the "ophthalmic pole" for centration on the visual axis, which are referred to as decentrations below, have no influence on spherical corrections is physically applicable only in certain cases, for example spherical corrections on spherical corneas. However, the visual physiology, inter alia, is not considered in this case. As a rule, decentrations may lead to a displacement in the physiological visual axis. When processing the visual impression in the brain, the eye is "rotated" by the eye muscles such that the light continues to fall on the point of sharpest vision, which in principle compensates the prismatic offset ("tip/tilt"). This may lead to problems in the case of binocular vision (stereopsis), for example, which problems are known from investigations in relation to insufficiently centrated spectacle lenses, for example. Particularly in the case of aspherical corrections on ellipsotoric corneas, which corresponds to the real, actual scenario, a decentration may also lead purely physically to a non-attainment of the sought-after correction. Accordingly, decentrations may have a significant influence on the results of "customized ablation", as this leads to the induction of higher aberrations ("night vision complaints", etc.) and hence also to an influence on the refractive result.

Hence, a centration that is as exact as possible is therefore paramount for a good result in the case of both topography and wavefront corrections.

Aberrations (or optical modes) couple under decentration. As a result of sphere and cylinder coupling to higher-order aberrations (coma, spherical aberration, higher-order astigmatism), including those occurring in natural (aspherical) eyes, decentrations in real eyes are often critical, even in the case of pure spherocylindrical corrections. By way of example, in the case of a decentration, coma couples to astigmatism and defocus or spherical aberration couples to coma, astigmatism and defocus. A few examples should be provided here, which initially only reveal the effects for primary aberrations (up to 4th order). The calculations follow from the coordinate transformation of optical modes:

A displacement of 0.25 μm with coma $Z(3,1)$ by 0.3 mm leads to a defocus of approximately $-\frac{1}{8}$ dpt.

A displacement of 0.25 μm with coma $Z(3,1)$ by 0.3 mm (horizontal/vertical) leads to a cardinal astigmatism $(Z(2,2)/Z(2,-2))$ of $\frac{1}{8}$ dpt.

A displacement of 0.5 μm with coma $Z(3,1)$ by 0.5 mm leads to a defocus of approximately $-0.3$ dpt.

A displacement of 0.4 μm with coma $Z(3,1)$ by 0.5 mm (horizontal/vertical) leads to a cardinal astigmatism $(Z(2,2)/Z(2,-2))$ of 0.3 dpt.

A displacement of 0.6 μm with spherical aberration $Z(4,0)$ by 0.4 mm leads to a defocus of approximately $-\frac{1}{8}$ dpt.

A displacement of 0.6 μm with spherical aberration $Z(4,0)$ by 0.4 mm (horizontal/vertical) leads to a cardinal astigmatism $(Z(2,2)/Z(2,-2))$ of approximately $\frac{1}{8}$ dpt.

Until now, only optical modes manifesting themselves in ablation profiles in the optical zone were considered. The transition zones have not yet been mentioned. However, in this context decentrations also mean that transition zones may reach into the optically active zone, especially in the case of hyperopia corrections. This may then lead to impairments (known as "night vision complaints post surgery;" this does not refer to night myopia), especially in the case of mesopic to scotopic light conditions, and may accordingly be accompanied by patient dissatisfaction.

Pupil centrations (centration in relation to the CSC, "corneal sighting center") can be brought about well and reliably in refractive surgery by means of eye tracking systems ("eye tracker") as integrated pupil recognition. However, this type of centration is not the preferred choice since it has in the meantime been settled in the art that a centration in relation to the ophthalmic pole (visual axis, coaxially sighted corneal light reflex, "CSCLR" condition, see below) or in relation to the vertex would be correct and preferable to a pupil centration. Experience has shown that small and medium myopia corrections are very uncritical in this case. Relatively large astigmatisms and myopia corrections and, in particular, hyperopia corrections are more difficult. This is because hyperopic eyes are typically characterized by a non-negligible angle between the pupil axis and the visual axis of the eye ("angle kappa"). In this case, corneal sighting center and ophthalmic pole are no longer sufficiently close together, leading to the difference between an "angle lambda" and an "angle kappa." As a rule, the angle lambda denotes the angle between the pupil axis or pupillary axis and the "line of sight" and the angle kappa denotes the angle between the pupil axis and the "visual axis." In this respect, see "Handbook of Visual Optics Vol. 1", CRC Press Taylor & Francis Group, Ed. Pablo Artal, Vol 1, Chapter 17 (by D. A. Atchison), or "Investigation of the isoplanatic patch and wavefront aberration along the pupillary axis compared to the line of sight in the eye", M. Nowakowski, M. Sheehan, D. Neal, A. V. Goncharov, Biomedical Optics Express, Vol. 3, 2. Moreover, the pupil and the pupil center are not fixed points which could unequivocally be provided with a marking. Both the pupil and the pupil center regularly vary with the lighting conditions.

Moreover, the pupil and the pupil center are not fixed points which could unequivocally be provided with a marking. Both the pupil and the pupil center regularly vary with the lighting conditions.

SUMMARY

It is therefore an object of the present disclosure to describe apparatuses and a method which address the aforementioned problems of currently used LVC systems. In particular, it is an object of the disclosure to describe apparatuses and methods for easy and reliable alignment or centration of the patient's eye in relation to the LVC system.

According to the disclosure, this object is achieved by systems and methods utilizing optical coherence tomography. Exemplary embodiments are specified in the dependent claims and in the description.

In a first aspect, the disclosure relates to a method for aligning a system for laser-based vision correction relative to a patient's eye to be treated. The method comprises providing specified preoperative measurement data which at least characterize predetermined structures of the patient's eye, the predetermined structures comprising a portion of the patient's eye to be treated. Furthermore, the method comprises measuring at least a portion of the predetermined structures of the patient's eye by means of an OCT system immediately before and/or during a treatment for vision correction for the patient's eye and providing OCT measurement data. Moreover, the method comprises comparing the OCT measurement data with the specified preoperative measurement data and providing comparison data, and determining a positioning and/or orientation of the portion of the patient's eye to be treated relative to the system and aligning the system relative to the patient's eye using the determined position and/or orientation of the portion of the patient's eye to be treated.

In a further aspect, the disclosure relates to a system for laser-based vision correction for a patient's eye. The system comprises an OCT system for measuring structures of the patient's eye immediately before and/or during a treatment for vision correction for the patient's eye and for providing OCT measurement data which characterize the measured structures of the patient's eye. Furthermore, the system comprises a control unit configured to compare the OCT measurement data provided by the OCT system with specified preoperative measurement data and to determine a positioning and/or orientation of the portion of the patient's eye to be treated relative to the system using comparison data from the comparison between the OCT measurement data provided by the OCT system and specified preoperative measurement data, and to align the system relative to the patient's eye using the determined position and/or orientation of the portion of the patient's eye to be treated.

In this case, OCT denotes optical coherence tomography. Accordingly, an OCT system in this case is a system designed to carry out optical coherence tomography-type measurements on a patient's eye. An OCT method accordingly is a method for carrying out an OCT measurement on one or more patient's eyes. In this case, the LVC system comprising an OCT system means that the OCT system forms a portion of the LVC system and, in particular, can be considered to be part of the latter.

In this case, specified preoperative measurement data are data which were determined during a measurement of the patient's eye prior to the vision treatment and independently of the alignment of the system relative to the patient's eye. By way of example, the specified preoperative measurement data may be available as diagnostic data, i.e., data determined during the diagnosis. In particular, the preoperative measurement data can be or may have been determined in a measurement carried out independently of the system for laser-based vision correction (LVC system). By way of example, the preoperative measurement data may have been determined using an OCT system that is separate from the LVC system. By way of example, the preoperative measurement data may be provided in the form of electronic data. By way of example, the system may comprise an interface to receive and/or retrieve specified preoperative measurement data. Additionally, the system may comprise a database with specified preoperative measurement data and/or be designed to be connected to such a database.

In this case, the predetermined structures of the patient's eye are structures of the patient's eye which are suitable and intended to be used for the determination and/or verification of the positioning and/or orientation of the patient's eye. In this case, the structures are predetermined to the effect of these also being measured using the OCT system of the LVC system in order to obtain comparable data records. In this case, the predetermined structures optionally are structures in the interior of the eye, which are characterizable by means of OCT measurements. By way of example, the predetermined structures may comprise a portion of, or the entire, anterior chamber of the eye, which can be characterized by means of OCT measurements. The measurement data obtained in the process can then be used for a determination and/or verification of the positioning and/or orientation of the eye.

In this case, a portion of the patient's eye to be treated is the portion which is treated, or provided for treatment, by means of the system for laser-based vision correction. In particular, the portion of the patient's eye to be treated may comprise, or consist of, the cornea of the patient's eye or a portion thereof. In particular, the treatment may comprise an ablation of a portion of the cornea by means of the system and/or a detachment of a lenticule from the interior of the cornea.

In this case, measuring at least a portion of the predetermined structures of the patient's eye by means of the OCT system immediately before and/or during a treatment for vision correction for the patient's eye means that the measurement is carried out simultaneously with the implementation of the treatment and/or has a direct temporal relationship with the treatment before the treatment, especially if the patient's eye is already at the envisaged position relative to the system for carrying out the treatment. Optionally, measuring the at least one portion of the predetermined structures of the patient's eye by means of the OCT system requires no change in the positioning and/or orientation of the patient's eye relative to the system that goes beyond a centration and/or alignment of the system. In this case, the provision of OCT measurement data means that the results of the measurement of the at least one portion of the predetermined structures of the patient's eye by means of the OCT system are provided, at least in part, immediately before and/or during a treatment for vision correction for the patient's eye, in particular to such an extent as is useful for the alignment of the system. Hence, the OCT measurement data may represent therapy data determined within the scope of a vision correction therapy.

In this case, the provision of comparison data means that the result of the comparison is made available to the system for further use, at least to such an extent as is useful for the alignment of the system. Optionally, the comparison data may comprise a lateral displacement $\Delta_{OCT}$ and/or a rotation $\Delta\beta_{OCT}$ of the OCT measurement data about the optical axis and/or a tilt $\Delta\alpha_{OCT}$ ("tip/tilt") in relation to the optical axis vis-à-vis the specified preoperative measurement data.

In this case, the alignment of the system comprises an adjustment of the system such that the system is centered on a position of the patient's eye that is desired for the vision treatment. Optionally, the alignment comprises no surgical or therapeutic step in this case. In particular, the alignment comprises a positioning and/or orientation of the system such that the latter is centered on the desired position of the eye, for example on the vertex or an offset position deviating therefrom. In this case, the system or a portion thereof, for instance a use part and/or an imaging optical unit or focusing optical unit of the system can be moved in order to adopt the desired orientation and/or positioning relative to the patient's eye. Alternatively or in addition, the patient or the patient's eye can be moved in order to adopt the desired positioning and/or orientation relative to the patient's eye.

The disclosure offers the advantage of enabling a particularly precise and reliable alignment of the system for aligning a system for laser-based vision correction relative to a patient's eye. By using OCT measurement data of the patient's eye obtained by means of the system and by comparing said data with specified preoperative measurement data, a very precise verification and/or adjustment of the positioning and/or orientation of the patient's eye is made possible.

The disclosure furthermore offers the advantage of being able to implement the alignment with great reliability independently of the individual properties of the patient's eye, in particular independently of the eye color of the patient's eye and the optical contrast of the iris arising therefrom and independently of the shape of the cornea. In this way, too, the cyclorotation of the eye can be reliably recognized and considered during the precise alignment, allowing the precision and reliability of the alignment to be improved even more.

Further, the disclosure offers the advantage of being able to be implemented in most or all conventional systems for laser-based vision correction, in particular in UV laser-based systems, which for instance have an excimer laser, and in picosecond or femtosecond laser-based systems.

The disclosure further enables a new form of tomographic centration which, in particular, is directly implantable in conjunction with a contact interface optionally utilized on the LVC system and the utilized system optics and an imaging objective, and which is useful as a visual centration aid. In this case, the method is based on the specified preoperative measurement data and allows and an alignment or centration on the basis of for example the anterior chamber tomography, that is to say an alignment or centration not purely based on the corneal surface.

This addresses further inaccuracies within the scope of centering UVL-LVC systems according to the prior art. However, such a system and method for referencing and determining offset coordinates for the scanning system, for example by way of an automated correction or a manual correction, are not restricted to a UV laser-based system for vision correction; instead, the principles according to the disclosure are also applicable to other systems for vision correction/for eye surgery, for example femtosecond and picosecond laser systems.

Optionally, the alignment of the system comprises a centration of the system on the vertex of the patient's eye. Optionally, the alignment of the system comprises a centration of the system on an offset position that deviates from the vertex and, optionally, a determination of offset coordinates of the offset position. This offers the advantage of the user being able to individually define the exact treatment position of the patient's eye when necessary. Optionally, the centration of the system on the offset position comprises a calculation of a centration-corrected fluence loss function. This offers the advantage of being able to precisely set the ablation and of being able to reduce a possible deviation of the ablation from the plan.

Optionally, the system can be aligned in manual, partially automated or fully automated fashion. By way of example, different degrees of automation may be provided depending on the system. Additionally, systems according to some exemplary embodiments may enable both an automated alignment and a partially automated and/or manual alignment. In this case, the manual alignment can be assisted by the system, in particular by the comparison according to the disclosure between OCT measurement data and specified preoperative measurement data.

Optionally, the predetermined structures of the patient's eye, which are characterized by the specified preoperative measurement data, and the at least one portion of the predetermined structures of the patient's eye, which is measured by means of the OCT system immediately before and/or during a treatment for vision correction, comprise at least a portion of the anterior chamber of the patient's eye. This offers the advantage of enabling a reliable verification on the basis of the anterior chamber of the patient's eye and, in particular, a unique assignment of the positioning and/or orientation of the anterior chamber to the orientation and/or positioning of the portion of the patient's eye to be treated, for instance the cornea, is possible. Moreover, this offers the advantage of keeping the measurement outlay for the measurement of the anterior chamber low and keeping the time required for the measurement short. Optionally, the portion of the patient's eye to be treated comprises at least one portion of the cornea.

Optionally, the method further comprises coupling the patient's eye to a contact interface of the system for laser-based vision correction. Optionally, the system further comprises a contact interface for coupling the patient's eye to the system. This allows a reliable fixation of the patient's eye relative to the system. In this case, the at least one portion of the predetermined structures of the patient's eye is optionally measured by means of the OCT system at least once before the patient's eye is coupled to the contact interface and at least once after the patient's eye has been coupled to the contact interface. This offers the advantage of being able to recognize and compensate possible changes in the positioning and/or orientation of the patient's eye as a result of docking to the contact interface, for example a contact glass, and/or of being able to consider these possible changes during the treatment.

Optionally, the method further comprises verifying the positioning and/or orientation of the portion of the patient's eye to be treated relative to the system by means of an eye tracker, the verification optionally being implemented continually during at least a part of the treatment for vision correction for the patient's eye. To this end, the system optionally further comprises an eye tracker for verifying the position and/or orientation of the patient's eye relative to the system, more particularly relative to the imaging optical unit. This offers the advantage of being able to reliably recognize and optionally compensate possible changes in the positioning and/or orientation of the patient's eye during the treatment and/or of being able to consider these changes in any other way during the treatment. In particular, the use of an eye tracker offers the advantage of not requiring a fixation of the patient's eye and, accordingly, a reliable alignment and/or positioning can also be implemented for those methods that do not contain a fixation of the patient's eye by means of a contact interface.

Optionally, the method comprises referencing an eye position determined by means of the eye tracker (for example, a pupil position and/or limbus position) using the OCT measurement data. This offers the advantage of allowing continual monitoring of the positioning and/or orientation of the patient's eye by means of the eye tracker and, moreover, of being able to attain a high degree of precision by way of initial referencing before the treatment and/or regular referencing during the treatment (for instance, during treatment breaks).

Optionally, the specified preoperative measurement data comprise preoperative OCT measurement data. This offers the advantage of being able to attain a high degree of comparability between the preoperative measurement data and the OCT measurement data provided by the system.

Optionally, the comparison data comprise a lateral displacement and/or a rotation and/or a tilt of the OCT measurement data relative to the preoperative OCT measurement data. This allows a possible deviation of the positioning and/or orientation of the patient's eye from the target position to be recognized and/or quantified with great precision and reliability.

By way of example, the rotation in this case may represent a rotation of the patient's eye according to the OCT measurement data relative to the patient's eye according to the preoperative measurement data. By way of example, the rotation can be determined as a rotation about a central axis or visual axis of the system and/or of an optical unit of the system and/or as a rotation about an optical axis of the eye according to the preoperative measurement data, said optical axis running centrally through the pupil. Alternatively or in addition, the rotation can be determined as a rotation about the keratometric axis of the patient's eye according to the preoperative measurement data, said keratometric axis running through the vertex.

Alternatively or in addition, a tilt of the eye according to the OCT measurement data can be determined relative to the eye according to the preoperative measurement data in one or more directions, especially in two directions. By way of example, a tilt of the optical axis of the eye and/or of the keratometric axis of the eye can be used to determine the tilt, said axes each being able to be determined from the comparison data.

Optionally, the system comprises a laser source for providing laser radiation for the treatment, the laser source optionally being designed to emit pulsed laser radiation and the laser source comprising an excimer laser and/or a picosecond laser and/or a femtosecond laser or being in the form of an excimer laser, picosecond laser and/or femtosecond laser. Consequently, depending on the sought-after treatment technique, the system can be equipped with a laser source suitable to this end. According to some exemplary embodiments, the system may comprise both a UV laser source and a picosecond and/or femtosecond laser. This enables the implementation of both ablation-based methods and methods for removing a lenticule.

Optionally, the system further comprises an imaging optical unit for focusing the laser radiation on the cornea of the patient's eye, the imaging optical unit being designed such that the imaging optical unit allows a detection of a back reflection of radiation radiated on the patient's eye by the imaging optical unit and at least partially reflected by the patient's eye, within an acceptance angle $\chi_{Max}$ of at least 2.5°. This offers the advantage of the back reflection of the radiation radiated on the patient's eye by the imaging optical unit and at least partially reflected by the patient's eye being able to be provided to the system for the analysis having been collected over a particularly large acceptance angle. This facilitates the implementation of the OCT measurement of the predetermined structures of the patient's eye and consequently facilitates the alignment of the system relative to the patient's eye. Optionally, the detection of the back reflection of radiation comprises a detection of a back reflection of an OCT beam radiated into the patient's eye by the imaging optical unit.

The imaging optical unit allowing a detection of the back reflection in an acceptance angle $\chi_{Max}$ of at least 2.5° means that the acceptance range detects rays of the back reflection at an angle to the optical axis of the imaging optical unit. Accordingly, an imaging optical unit with an acceptance angle of 2.5° for example can detect optical rays of the back reflection that are reflected from the cornea to the imaging optical unit within a light cone with an opening angle of 5° with respect to the direction of incidence (i.e., with an opening angle of 2.5° between the lateral face of the light cone and the center line of the light cone), and so these rays can be collected by the imaging optical unit and can be used by the system.

Optionally, the imaging optical unit is designed such that the acceptance angle $\chi_{Max}$ is greater than 5°, optionally greater than 10°, optionally greater than 15°, optionally greater than 25° and optionally greater than or equal to 37°. This increases the range in which the radiation reflected by the eye can be collected and used for the OCT measurement. Consequently, the measurable region of the patient's eye is increased as a result and the precision and the reliability of the alignment is improved.

Optionally, the imaging optical unit is designed as, or comprises, a microscope optical unit. In this case, the imaging optical unit optionally has an optical opening and a given working distance, in the case of which a diameter of the optical opening is greater than or equal to the given working distance. Optionally, the imaging optical unit has an optical opening with a diameter of at least 50 mm, optionally of at least 60 mm. Optionally, the imaging optical unit further has a working distance of less than 50 mm and optionally of less than or equal to 40 mm. This offers the advantage of being able to provide a particularly large acceptance angle.

The features and exemplary embodiments specified above and explained below should not only be considered to be disclosed in the respective explicitly mentioned combinations in this case, but are also comprised by the disclosure in other technically advantageous combinations and embodiments.

Further details and advantages of the disclosure should now be explained in more detail on the basis of the following examples and exemplary embodiments with reference being made to the drawings.

BRIEF DESCRIPTION OF THE DRAWINGS

The disclosure will now be described with reference to the drawings wherein.

DESCRIPTION OF EXEMPLARY EMBODIMENTS

The same or similar elements in the various exemplary embodiments are denoted by the same reference signs in the following figures for reasons of simplicity.

Figure 1:
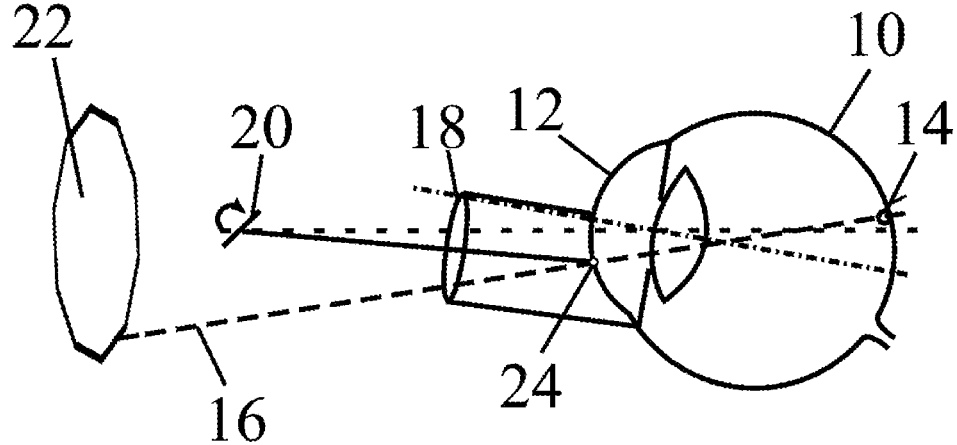
FIG. 1 shows a schematic representation of an unsuitably placed ablation profile.

FIG. 1 shows a schematic representation of the principle of how prismatic correction errors (tip/tilt) arise according to a conventional centration method when the patient does not fixate on the center of the fixation object or "fixation cloud." In this case, FIG. 1 depicts a patient's eye 10 with cornea 12 and fovea 14, and the optical axis 16 of the patient's eye or the visual axis 16, an ablation profile 18, a scanning system 20 and a fixation element 22, on which the patient should fixate with their gaze. The visual axis 16 intersects the cornea 12 at the ophthalmic pole 24 (point of intersection of the visual axis with the anterior corneal surface under patient fixation).

If the patient does not fixate their eye 10 on the center of the fixation element 22 as envisaged but, for example, on an edge region of the fixation element 22, this may have as a consequence that the ablation profile 18 is not correctly applied along the necessary treatment axis (e.g., along the visual axis 16; defined by the ophthalmic pole (OP) and point of the fixation element 22 fixated by the patient's eye 10 and hence not orthogonal to the visual axis 16). To provide a better overview, the relationships are depicted with much exaggeration in FIG. 1.

Therefore, avoiding the generation of such prismatic aberrations should be ensured when a patient's eye is treated using an LVC system. If this is not ensured, this may lead to the unwanted case of the ablation profiles 18 not being applied in the correct plane, that is to say not on the surface normal, i.e., perpendicular to the visual axis 16. This may be promoted by virtue of the patient preferably fixating in a largely fixed but "incorrect" direction, that is to say, e.g., permanently looking in a fixed direction that does not correspond to the center of the fixation element 22 (depending on refractive deficit and treatment duration, the patient can no longer see the fixation target in focus during the operation).

Figure 2:
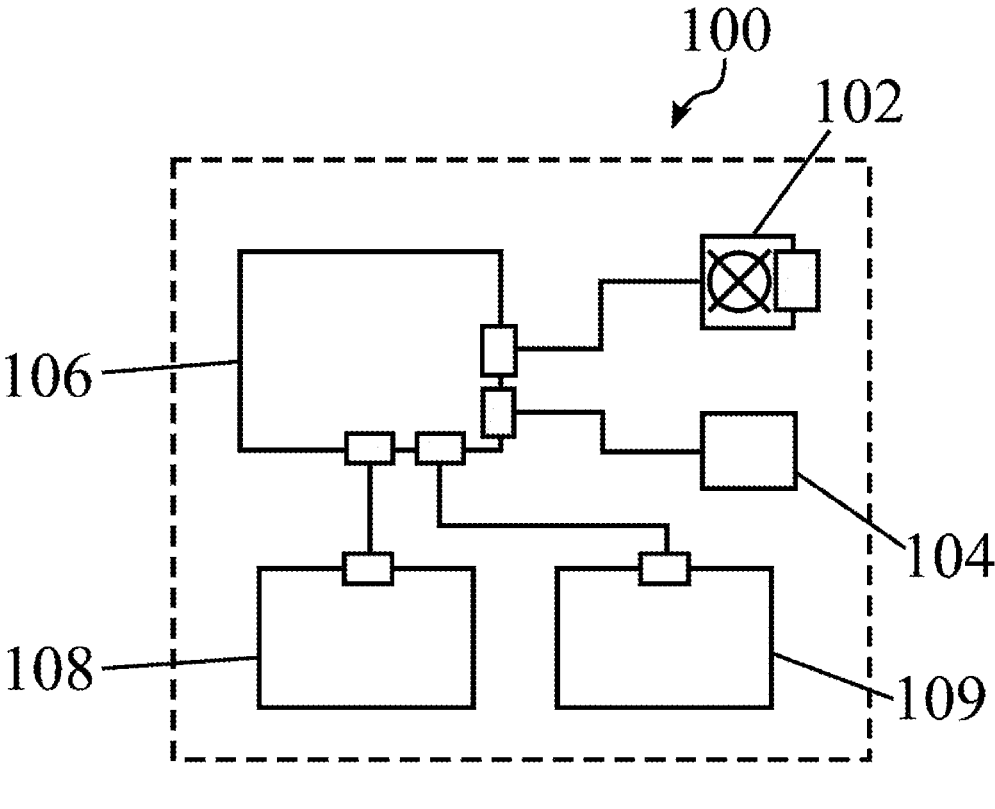
FIG. 2 shows a schematic representation of an LVC system according to an exemplary embodiment.

FIG. 2 shows a schematic representation of an LVC system 100 according to an exemplary embodiment of the disclosure. The LVC system 100 comprises a laser source 102, a scanning system 104, a control unit 106, as well as a planning unit 108 and an OCT system 109. For data exchange between the control unit 106 and the laser source 102, the scanner 104 and the planning unit 108 and also the OCT system 109, the control unit 106 has interfaces (represented by boxes on the control unit S), by means of which the data line can be transferred by way of cables. The planning unit 108 likewise comprises an interface (depicted as a box on the planning unit P) for data exchange with the control unit 106. A wireless transfer is likewise possible. The planning unit 108 has a computing unit (not depicted here), by means of which the planning data are calculated. The terms scanner and scanning system are used synonymously in this disclosure.

Figure 3A:
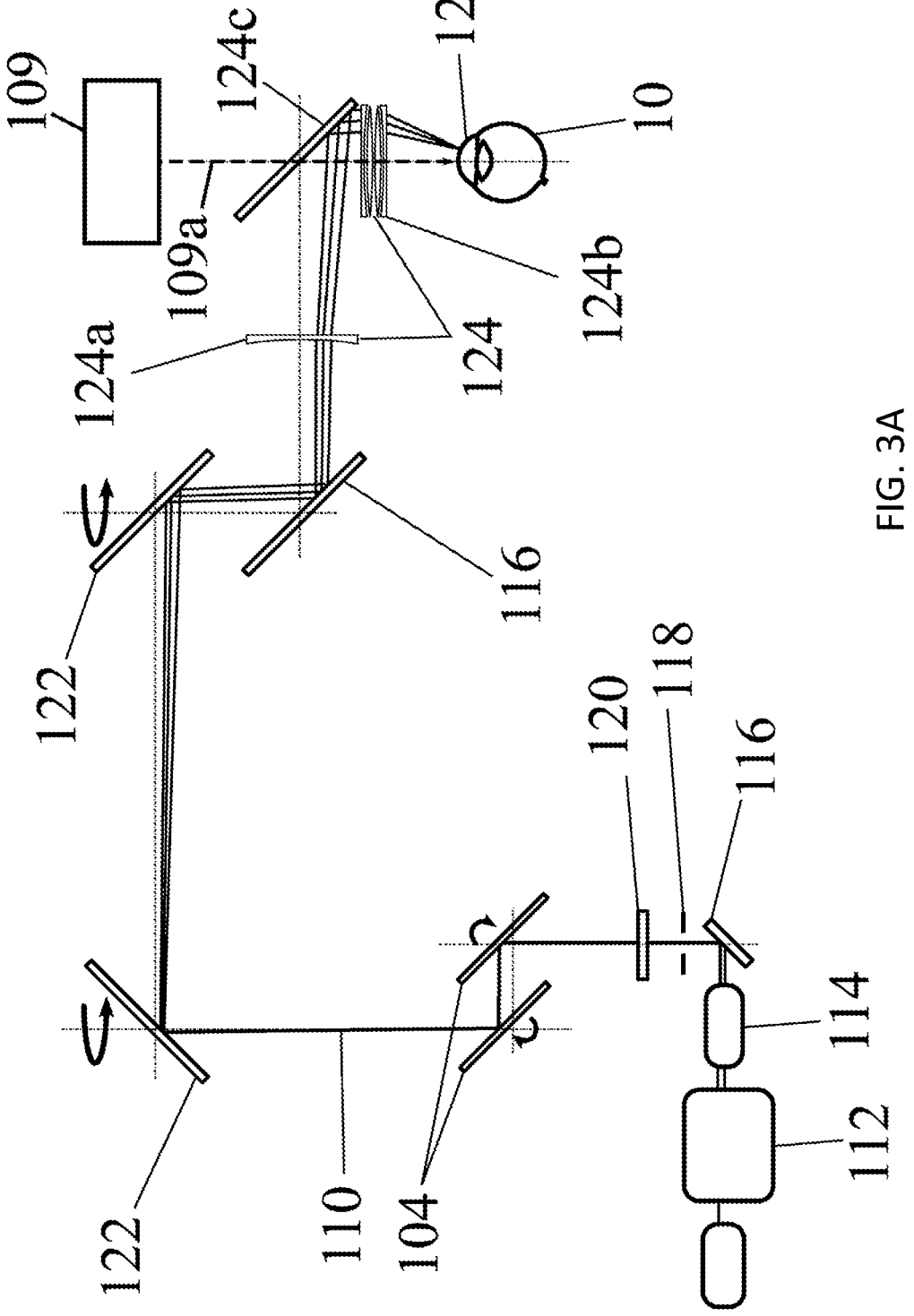
FIG. 3A shows a beam profile of an LVC system according to an exemplary embodiment.

FIG. 3A shows a basic arrangement of the optical beam path of an exemplary embodiment of an LVC system 100, in particular of the use part of the LVC system 100, in an exemplary fashion. A laser beam 110 is provided by a UV laser or a femtosecond laser or a picosecond laser 112 as a laser source. The laser beam 110 is attenuated by an (optional) optical attenuator 114, deflected by a deflector 116, is incident on a stop (or a pinhole) 118 and subsequently reaches the beam shaper 120. The latter serves to shape the beam of the raw laser beam into a Gaussian or super-Gaussian pulse fluence distribution. By way of the scanning system 104, the laser beam 110 can be deflected laterally in the x- and y-directions (depicted by way of bent arrows). From here, the laser beam 110 is guided in a first articulated arm. In the exemplary embodiment shown, the latter is movably connected to a base unit (not plotted) by way of a first rotary joint 122 (symbolized by an axis of rotation and a rotation arrow). The base unit comprises the laser source 102 or the excimer laser 112, the optical attenuator 114, the stop 118 (and the deflector 116 which is situated in the beam path between the optical attenuator 114 and the stop 118), the beam shaper 120 and the scanning system 104. The first articulated arm is movably connected to a second articulated arm by way of a second rotary joint 122 (symbolized by an axis of rotation and a rotation arrow) on the side distant from the base unit. The laser beam 110 is guided into the second articulated arm via two further deflectors 116 by way of the second rotary joint 122. Even further rotary joints may additionally be formed according to further exemplary embodiments. From there, the laser beam 110 is steered in the direction of the patient's eye 10 by way of a further deflector 116. In this case, the laser beam 110 is focused on the cornea 12 of the patient's eye 10 by way of a focusing optical unit or imaging optical unit 124. In this case, the imaging optical unit 124 has a two-part structure. A deflector 124c is situated in the beam path between the first lens group 124a and the second lens group 124b. The required lenses of the two lens groups 124a, 124b are only depicted schematically. In this case, the imaging optical unit 124 is embodied so that the latter has an acceptance angle of at least 2.5° for detecting a back reflection of radiation radiated on the cornea by the imaging optical unit. According to the exemplary embodiment shown, the deflector also serves to couple an OCT laser beam 109a into the patient's eye by the imaging optical unit 124 and to guide the reflected back reflection collected by the imaging optical unit 124 back to the OCT system 109.

Figure 3B:
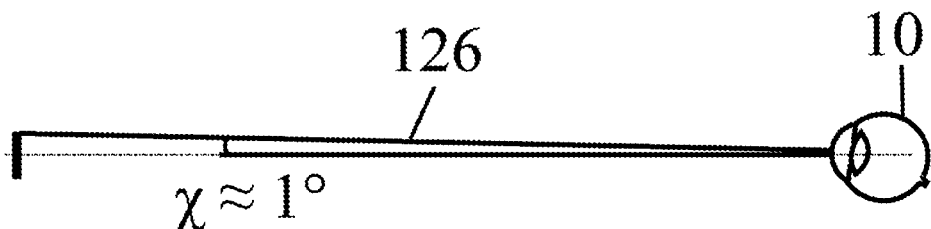
FIG. 3B shows an exemplary acceptance angle of a conventional LVC system.
Figure 3C:
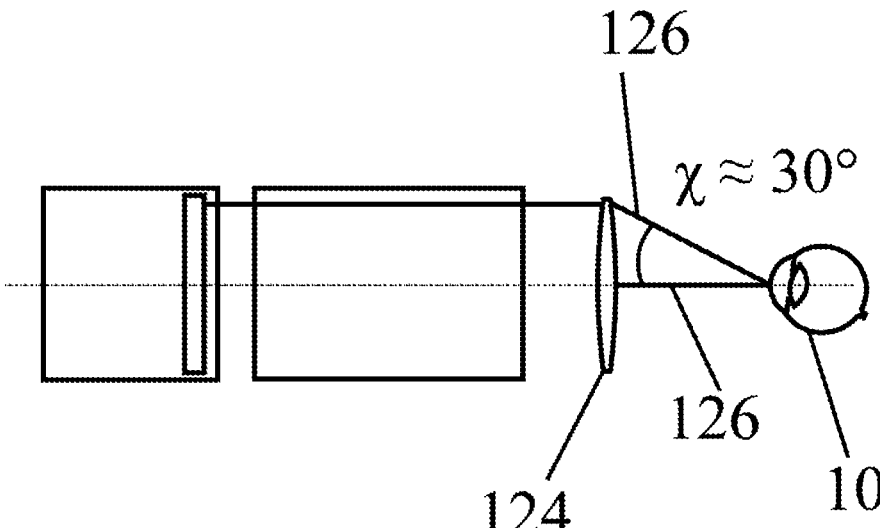
FIG. 3C shows an exemplary acceptance angle of an LVC system according to an exemplary embodiment.

In schematic representations, FIGS. 3B and 3C elucidate a conventional LVC system (FIG. 3B) with an acceptance angle for back reflections 126 of approximately 1° in comparison with an LVC system according to an exemplary embodiment of the disclosure with an acceptance angle of approximately 30°.

Figure 4:
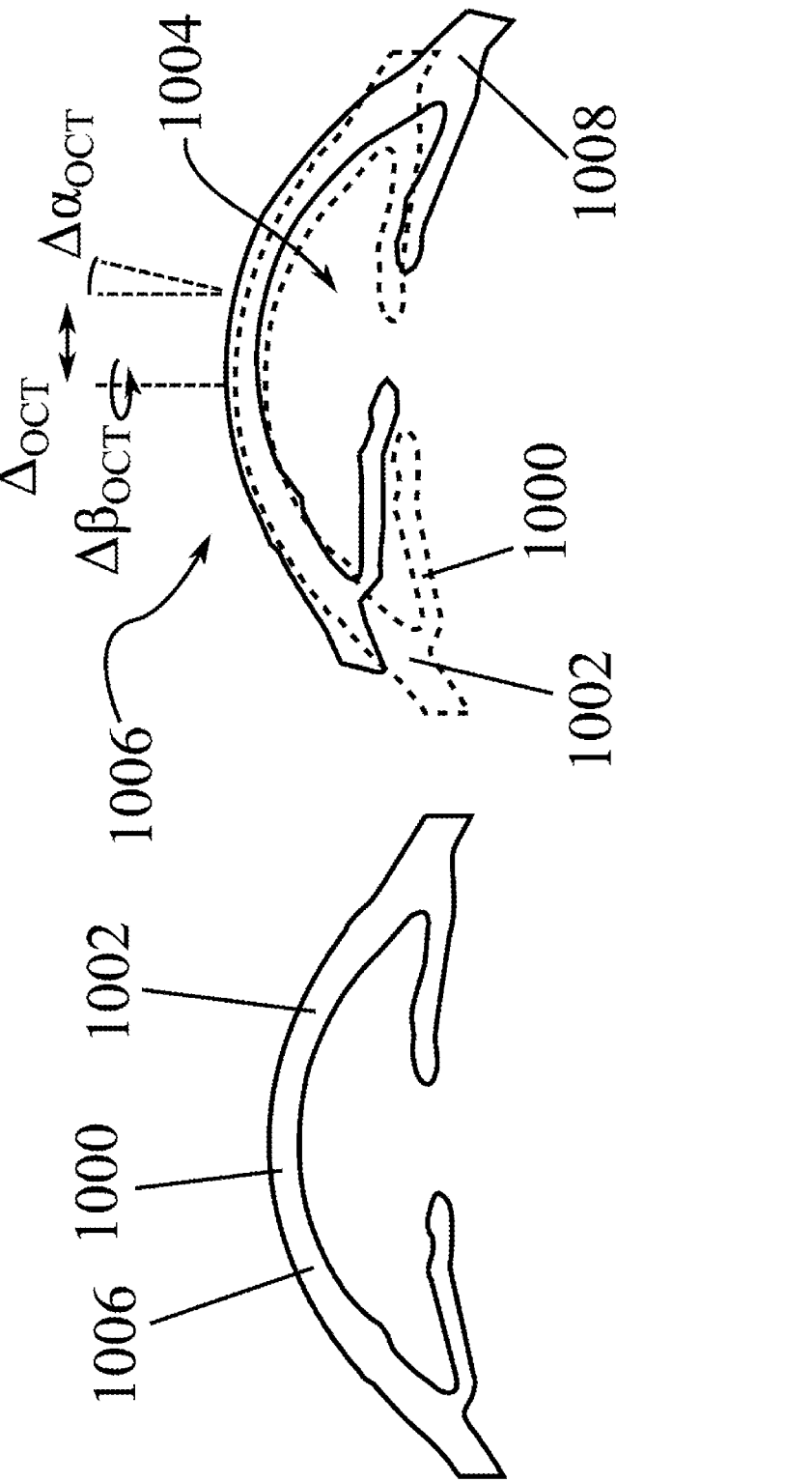
FIG. 4 shows visualizations of OCT measurement data and specified preoperative measurement data for the purposes of explaining the principle of a method for aligning an LVC system relative to patient's eye according to an exemplary embodiment.

With reference to FIG. 4, the principle of a method for aligning an LVC system relative to a patient's eye according to an exemplary embodiment is described below.

In this case, the left partial image schematically and by way of example shows specified preoperative measurement data 1000 of predetermined structures 1002 of the patient's eye 10. In this case, the predetermined structures comprise the anterior chamber 1004 of the patient's eye 10 and also the portion 1006 of the patient's eye 10 to be treated, which according to the explained exemplary embodiment comprises a portion of the cornea 12 of the patient's eye 10.

In this case, the algorithms of the LVC system according to the exemplary embodiment recognize the contour of the anterior chamber (edging in the partial images of FIG. 4). Then, this contour serves as a reference (OCT reference contour) for the contact interface positioning and centration when aligning or centering the LVC system relative to the patient's eye, in particular during the contact interface adaptation to the patient's eye should a contact interface be used.

In this case, the specified preoperative measurement data 1000 serve as reference data and are provided by suitable diagnostic equipment, for example by means of an OCT system (e.g., MS 39 CSO, not shown) that is independent of the LVC system. The specified preoperative measurement data 1000 may be provided as preoperative OCT measurement data 1000 in the process and are used for the alignment of the LVC system 100.

Provided the exemplary embodiment provides for coupling and fixating of the patient's eye to a contact interface, the preoperative OCT measurement data can be used as a reference for the contact interface positioning and centration. To this end, the preoperative OCT measurement data are provided to the LVC system.

By way of example, the LVC system may provide for a determination and use of the OCT contour of the anterior chamber and/or of the cornea (see contour line) on the basis of the preoperative OCT measurement data. According to the explained exemplary embodiment, the LVC system then, by means of its own OCT system, measures at least a portion of the predetermined structures of the patient's eye immediately before and/or during a treatment for the vision correction for the patient's eye and provides appropriate OCT measurement data 1008. This is optionally implemented using identical OCT technology or in the same manner in situ, that is to say just before and after implementation of a contact interface adaptation, with OCT measurements being carried out repeatedly and the OCT contour optionally likewise being determined. Accordingly, the system-inherent OCT system can have a similar or identical design to the OCT system used to determine the specified preoperative measurement data 1000.

Then, the LVC system compares the OCT measurement data with the specified preoperative measurement data and a provides comparison data. Moreover, the LVC system implements a determination of a positioning and/or orientation of the portion of the patient's eye to be treated relative to the system and an alignment of the system relative to the patient's eye using the determined position and/or orientation of the portion of the patient's eye to be treated. In this case, the alignment can be implemented in fully or partially automated fashion by the LVC system, or at least partially in manual fashion by the user.

For the purposes of the manual alignment or centration in relation to the OCT data, the specified preoperative measurement data 1000 and the measurement data of the current (in situ) OCT measurement by the LVC system, that is to say the OCT measurement data, are visualized on a display for the user, to be precise in relation to the same coordinate reference ("reference coordinates system"). This is depicted in the right partial image of FIG. 4. By way of suitable application software, the specified preoperative measurement data and the OCT measurement data 1008 can be represented together, optionally in overlaid form, as two layers in order to facilitate the manual alignment and/or the monitoring of the automated alignment for the user.

For manual alignment or centration purposes, the user is able to displace the optical unit for applying the laser radiation to the patient's eye, which may, for example, be in the form of, or comprise, a microscope optical unit, laterally over the eye in the xy-plane (for instance by a displacement of a use part in which the optical unit is integrated) such that the two OCT images, that is to say the visual representation of the specified preoperative measurement data 1000 and of the OCT measurement data 1008, have the smallest possible deviation from one another in terms of their positioning and/or orientation. For further assistance of the user, directional indicators may optionally be depicted on a display for visualization purposes or, for example, the display of a lateral displacement $\Delta_{OCT}$ and/or a rotation $\Delta\alpha_{OCT}$ of the visualization of the OCT measurement data 1008 vis-à-vis the specified preoperative measurement data 1000. Under patient fixation, both variables, that is to say the lateral displacement $\Delta_{OCT}$ and/or a rotation $\Delta\alpha_{OCT}$ and/or a tilt, should together tend to zero with an improvement in the centration during the lateral displacement of the use part in the xy-plane for manual centration purposes.

To also allow the use of OCT systems with a limited bandwidth, it is possible to restrict the repetition rate of the data for the comparison with the previously acquired data. In particular, the OCT scanning procedure can be intermittently restricted to a characteristic portion of the coordinates, optionally after sighting and assessing the diagnostic data. Initially, a complete detection of the anterior chamber is advantageous and a detection of the characteristic, preselected portions, that is to say the specified preoperative measurement data, is necessary to this end. This can be implemented in manual, partially automated or fully automated fashion by way of suitable image recognition methods. Subsequently, it is possible thereafter to dispense with a renewed complete OCT measurement of the entire anterior chamber and instead it is possible to only capture portions and carry out a comparison between diagnostic data and therapy data, that is to say between the specified preoperative measurement data and OCT measurement data. Since this may significantly reduce the number of B-scans required, this is advantageous for the bandwidth of the therapy data acquisition and is accordingly advantageous for the use of OCT systems with a reduced bandwidth. Following a successful centration of the portion data with respect to one another, it is optionally possible to yet again implement the slow scan of all structures for the final check.

According to a further exemplary embodiment, the method comprises the automated provision of offset coordinates from the lateral displacement $\Delta_{OCT}$ and the rotation $\Delta\beta_{OCT}$ and the tilt $\Delta\alpha_{OCT}$ and optionally a tilt. In this case, a set of offset coordinates is generated for the purposes of aligning or centering the LVC system on a point that deviates from, e.g., the vertex and/or the pupil center of the cornea, for instance in order to calculate a centration-corrected fluence loss function using said coordinates. This provides the option of reducing a possible deviation between the intended and actual ablation of the cornea.

In a further exemplary embodiment variant, the comparison of the OCT measurement data with the specified preoperative measurement data may also be carried out in a contactless method without a contact interface, for example optionally in combination with an eye tracking system. In this case, there is the option of updating the OCT beam by way of the tracking signal of the eye tracker in order to compensate possible slight eye movements. Alternatively, updating of the OCT beam can be dispensed with if the OCT B-scan data are corrected using the simultaneously acquired eye tracking coordinates.

In both variants, the center determined by means of the OCT measurement or tomography, that is to say the point on which the system was centered by means of the alignment, can be referenced to the pupil center or preferably the limbus center and/or to the iris, and this can thereafter be updated during the ablation process with a high bandwidth by the eye tracker.

Moreover, in this case, the OCT system may also be optionally used to monitor the correct z-distance between cornea and laser system following the tomographic centration. In particular, this is advantageous if a contact interface cannot be used for anatomical, medical or other reasons. Since a displacement of the eyes along the axis of symmetry of the optical unit significantly influences the points of incidence of the treatment light in the convergent focal field, a detection of this displacement is advantageous in this case. By way of example, the z-coordinate can then be measured by 2-D eye tracking at the coordinate of the treatment center. In the case of a separate scanning system for the OCT beam, this is very easy and possible with a high bandwidth. If the OCT beam is guided over the scanners of the treatment laser, an intermediate verification of the z-position is optionally possible between single shots or statistically at the times when ablation pulses are shot into the treatment center. The surface of the cornea in the treatment center or, preferably, the interface not impaired by the treatment and located between the endothelium and the aqueous humor on the back side of the treatment center can serve as the measurement signal.

The aforementioned features of the disclosure, which are explained in various exemplary embodiments, can be used not only in the combinations specified in an exemplary manner but also in other combinations or on their own, without departing from the scope of the present disclosure.

A description of an apparatus relating to method features is analogously applicable to the corresponding method with respect to these features, while method features correspondingly represent functional features of the apparatus described.

Moreover, the disclosure comprises the subject matter of the following clauses:

Clause 1. A UV laser-based system for vision correction (UVL-LVC system), comprising:

a UV laser source which emits preferably pulsed laser radiation, a scanning system for lateral scanning of the laser radiation in the x- and y-directions, and preferably also in the z-direction, an imaging optical unit for focusing the preferably pulsed laser radiation on the cornea of a patient's eye, an OCT system for measuring or imaging at least partial structures of a patient's eye, preferably at least portions of the structure of the anterior chamber of the patient's eye, a control unit, an interface for transferring preoperative data or image representations of at least the partial structures of a patient's eye, preferably at least the portions of the structure of the anterior chamber of the patient's eye, from diagnostic equipment comprising an OCT system, wherein the control unit or a planning unit connected to the control unit is configured to compare the data or image representations determined by the OCT system with the preoperative data or image representations and to determine offset coordinates for the scanning system therefrom, for an automated correction by way of a scanner allowance or for a manual correction or an automated correction by alignment.

Clause 2. The UVL-LVC system according to clause 1, the imaging optical unit of which comprises a microscope optical unit for focusing the preferably pulsed laser radiation on the cornea of a patient's eye, the optical opening of said optical unit is designed such that an acceptance angle $\chi_{Max}$ for back reflections detectable by the UVL-LVC system according to the disclosure of greater than 15°, preferably greater than 25° and particularly preferably greater than or equal to 37° is achievable.

Clause 3. The UVL-LVC system according to clause 1 or 2, the optical opening of which is greater than 50 mm, preferably greater than or equal to 60 mm, and the working distance of which is less than 50 mm, preferably less than or equal to 40 mm.

Clause 4. The UVL-LVC system according any one of clauses 1 to 3, the imaging optical unit of which contains an objective for imaging the laser radiation in a focal field, with the objective comprising a lens formed to provide a convergent focal field.

Clause 5. The UVL-LVC system according to any one of clauses 1 to 4, furthermore comprising a contact interface for coupling the patient's eye to the UVL-LVC system.

Clause 6. The UVL-LVC system according to any one of clauses 1 to 5, configured to determine the offset coordinates for the scanning system for the automated correction by way of a scanner allowance or for the manual correction or automated correction by alignment from the lateral displacement and/or the rotation of the partial structures of the patient's eye, preferably of the portions of the structure of the anterior chamber of the patient's eye, measured or imaged by the OCT system of the UVL-LVC system in relation to the partial structures of the patient's eye, preferably the portions of the structure of the anterior chamber of the patient's eye, measured or imaged by the diagnostic equipment comprising an OCT system.

Clause 7. The UVL-LVC system according to any one of clauses 1 to 6, the control unit of which or the planning unit of which connected to the control unit comprises an algorithm for OCT contour determination.

Clause 8. The UVL-LVC system according to any one of clauses 1 to 7, which in the case of an automated correction has an algorithm for calculating a centration-corrected fluence loss function.

Clause 9. The system according to clauses 1 to 8, moreover containing an eye tracking system which determines the two-dimensional coordinates of the pupil center and preferably the limbus center with a high refresh rate (500 Hz, preferably more than 1000 Hz).

Clause 10. A method for centering a UVL-LVC system, wherein preoperative data or image representations of at least partial structures of a patient's eye, preferably at least portions of the structure of the anterior chamber of the patient's eye, are generated by diagnostic equipment comprising an OCT system, data or image representations of at least the partial structures of the patient's eye, preferably at least the portions of the structure of the anterior chamber of the patient's eye, are generated in turn by an OCT system of the UVL-LVC system, offset coordinates for the scanning system are determined for the automated correction or for the manual correction from the comparison of both sets of data or image representations, and the UVL-LVC system is centered in relation to the patient's eye by means of these offset coordinates.

Clause 11. The method for centering a UVL-LVC system according to clause 10, wherein data or image representations of at least the partial structures of the patient's eye, preferably of at least the portions of the structure of the anterior chamber of the patient's eye, are produced by the OCT system of the UVL-LVC system before, during and/or optionally after the patient's eye has been coupled to the UVL-LVC system by means of a contact interface.

Clause 12. The method for centering a UVL-LVC system according to clause 10 or 11, wherein an algorithm for calculating a centration-corrected fluence loss function is used during an automated correction.

Clause 13. The method according to clause 10 or 11 or 12, wherein the determination of the offset position by way of an OCT comparison is implemented simultaneously with a tracking of the eye by means of an eye tracker, in such a way that even after the tomographic centration the offset position and the laser pulse positions centered thereon are captured and updated by way of the tracking system in the case of eye movements.

Clause 14. The method according to clauses 10 to 13, wherein the 2-D coordinates of an eye tracking system are supplemented with z-coordinates obtained by one or more OCT A-scans, the OCT measuring beam preferably being steered to the tracked treatment center and the relative position of the corneal front side being determined as a reference position, but with the back side of the cornea preferably being used to this end.

LIST OF REFERENCE SIGNS

10 Patient's eye
12 Cornea
14 Fovea
16 Visual axis/optical axis of the eye
18 Ablation profile
20 Scanning system
22 Fixation element
24 Ophthalmic pole
100 (LVC) system
102 Laser source
104 Scanner or scanning system
106 Control unit
108 Planning unit
109 OCT system
109a OCT laser beam or OCT beam
110 Laser beam
112 Laser
114 Attenuator
116 Deflector
118 Stop
120 Beam shaper
122 Rotary joint
123 Use part
124 Imaging optical unit
124a First lens group of the imaging optical unit
124b Second lens group of the imaging optical unit
124c Deflector

20

126 Back reflection
$\chi$ Opening angle of the back reflection
$\chi_{Max}$ Maximum detectable opening angle of the back reflection or acceptance angle of the imaging optical unit
1000 (Visualization of the) preoperative measurement data
1002 Predetermined structures
1004 Anterior chamber of the patient's eye
1006 Portion of the patient's eye to be treated
1008 (Visualization of the) OCT measurement data
$\Delta_{OCT}$ Lateral displacement
$\Delta\alpha_{OCT}$ Tilt
$\Delta\beta_{OCT}$ Rotation

The invention claimed is:

1. A method for aligning a system for laser-based vision correction relative to a patient's eye to be treated, the method comprising:

providing specified preoperative measurement data which at least characterize predetermined structures of the patient's eye, the predetermined structures including a portion of the patient's eye to be treated, wherein the provided specified preoperative measurement data are based on a measurement carried out independently of the system for laser-based vision correction;

measuring at least a portion of the predetermined structures of the patient's eye with an Optical Coherence Tomography (OCT) system immediately before and/or during a treatment for vision correction for the patient's eye and providing OCT measurement data;

comparing the OCT measurement data with the specified preoperative measurement data and providing comparison data; and determining a positioning and/or orientation of the portion of the patient's eye to be treated relative to the system using the comparison data, and aligning the system relative to the patient's eye using the determined position and/or orientation of the portion of the patient's eye to be treated.

2. The method as claimed in claim 1, wherein the alignment of the system comprises a centration of the system on a vertex of the patient's eye.

3. The method as claimed in claim 1, wherein the alignment of the system comprises a centration of the system on an offset position that deviates from a vertex of the patient's eye and, optionally, a determination of offset coordinates of the offset position.

4. The method as claimed in claim 3, wherein the centration of the system on the offset position comprises a calculation of a centration-corrected fluence loss function.

5. The method as claimed in claim 1, wherein the system is aligned in manual, partially automated or fully automated fashion.

6. The method as claimed in claim 1, wherein the predetermined structures of the patient's eye, which are characterized by the specified preoperative measurement data, and the at least one portion of the predetermined structures of the patient's eye, which is measured by means of the OCT system immediately before and/or during a treatment for vision correction, comprise at least a portion of an anterior chamber of the patient's eye.

7. The method as claimed in claim 1, wherein the portion of the patient's eye to be treated comprises at least a portion of a cornea of the patient's eye.

8. The method as claimed in claim 1, further comprising: coupling the patient's eye to a contact interface of the system for laser-based vision correction, wherein the at least one portion of the predetermined structures of the patient's eye is measured by means of the OCT system at least once before the patient's eye is coupled to the contact interface and at least once after the patient's eye has been coupled to the contact interface.

9. The method as claimed in claim 1, further comprising:
verifying the positioning and/or orientation of the portion of the patient's eye to be treated relative to the system with an eye tracker, the verification optionally being implemented continually during at least a part of the treatment for vision correction for the patient's eye.

10. The method as claimed in claim 9, further comprising:
referencing an eye position determined with the eye tracker using the OCT measurement data, the determined eye position optionally including, or corresponding to, a pupil position and/or a limbus position.

11. The method as claimed in claim 1, wherein the specified preoperative measurement data comprise preoperative OCT measurement data.

12. The method as claimed in claim 11, wherein the comparison data comprise a lateral displacement ($\Delta_{OCT}$) and/or a rotation ($\Delta\beta_{OCT}$) and/or a tilt ($\Delta\alpha_{OCT}$) of the OCT measurement data relative to the preoperative OCT measurement data.

13. The method as claimed in claim 1, wherein the preoperative measurement data are provided in the form of electronic data.

14. The method as claimed in claim 1, wherein the specified preoperative measurement data are retrieved or received via an interface of the system for laser-based vision correction.

15. The method according to claim 1, wherein the specified preoperative measurement data are retrieved or received from a database connected to the system for laser-based vision correction.

16. A system for laser-based vision correction for a patient's eye, the system comprising
an Optical Coherence Tomography (OCT) system for measuring predetermined structures of the patient's eye immediately before and/or during a treatment for vision correction for the patient's eye and for providing OCT measurement data which characterize the measured predetermined structures of the patient's eye; and
a control unit configured to compare the OCT measurement data provided by the OCT system with specified preoperative measurement data and to determine a positioning and/or orientation of a portion of the patient's eye to be treated relative to the system using comparison data from the comparison between the OCT measurement data provided by the OCT system and the specified preoperative measurement data, and to align the system relative to the patient's eye using the determined position and/or orientation of the portion of the patient's eye to be treated;
wherein the provided specified preoperative measurement data are based on a measurement carried out independently of the system for laser-based vision correction.

17. The system as claimed in claim 16, further comprising a laser source for providing laser radiation for the treatment, the laser source optionally being configured to emit pulsed laser radiation and the laser source including an excimer laser and/or a picosecond laser and/or a femtosecond laser or being in the form of an excimer laser, picosecond laser and/or femtosecond laser.

18. The system as claimed in claim 17, further comprising:
an imaging optical unit for focusing the laser radiation on the cornea of the patient's eye, the imaging optical unit being configured such that the imaging optical unit allows a detection of a back reflection of radiation radiated on the patient's eye by the imaging optical unit and at least partially reflected by the patient's eye, within an acceptance angle $\chi_{Max}$ of at least 2.5°.

19. The system as claimed in claim 18, wherein the system, and in particular the imaging optical unit, are configured such that the acceptance angle $\chi_{Max}$ is greater than 5°.

20. The system as claimed in claim 18, wherein the imaging optical unit is in the form of, or comprises, a microscope optical unit.

21. The system as claimed in claim 18, wherein the imaging optical unit has an optical opening and a given working distance, a diameter of the optical opening being greater than or equal to the given working distance.

22. The system as claimed in claim 18, wherein the imaging optical unit has an optical opening with a diameter of at least 50 mm, and wherein the imaging optical unit has a working distance of less than 50 mm.

23. The system as claimed in claim 18, wherein the detection of the back reflection of radiation comprises a detection of a back reflection of an OCT beam radiated into the patient's eye by the imaging optical unit.

24. The system as claimed in claim 16, further comprising a contact interface for coupling the patient's eye to the system.

25. The system as claimed in claim 16, further comprising an eye tracker for verifying the position and/or orientation of the patient's eye relative to the system, optionally relative to the imaging optical unit.

* * * * *